April 4, 1972 C. J. HALKA Plant Pat. 3,096
HONEY-LOCUST TREE
Filed March 3, 1970
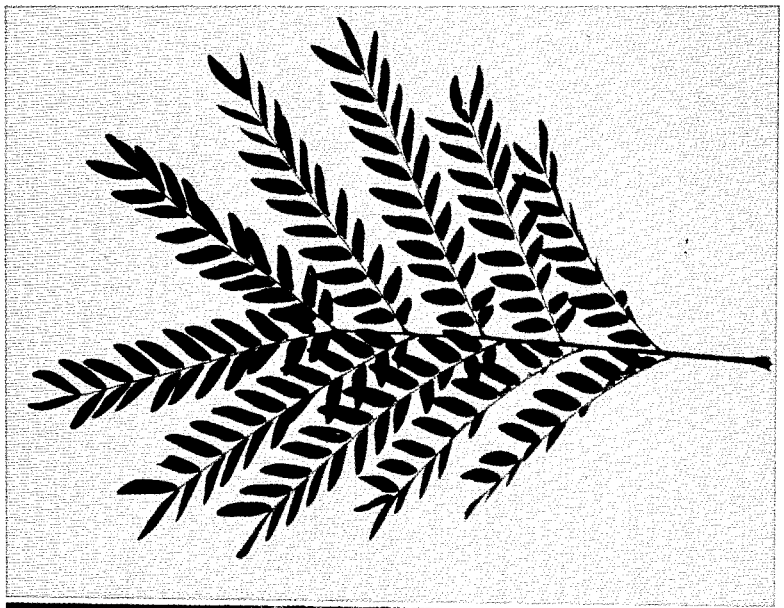
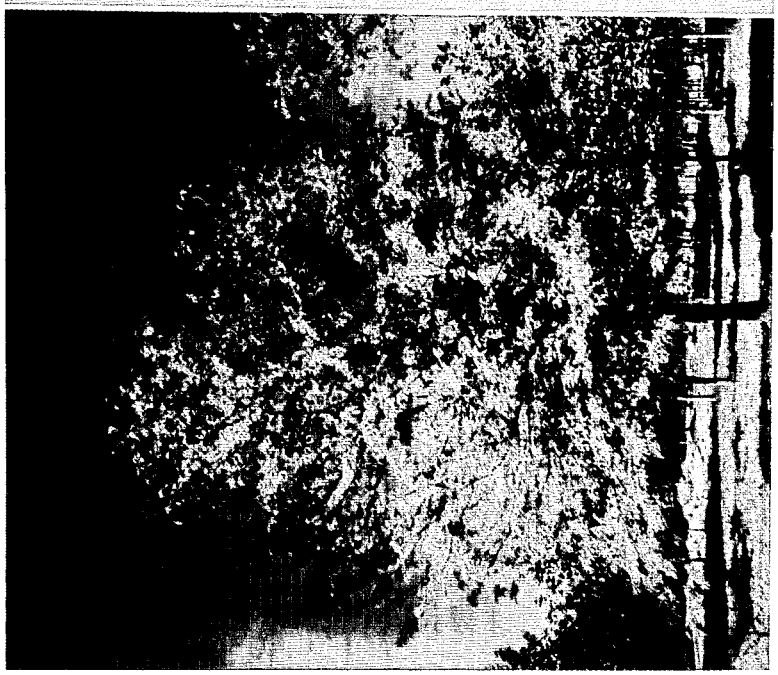
Inventor.
Chester J. Halka
By: Robb & Robb
Attorneys.

United States Patent Office

Plant Pat. 3,096
Patented Apr. 4, 1972

3,096
HONEY-LOCUST TREE

Chester J. Halka, Englishtown, N.J., assignor to Frank J. Schmidt & Son Co., Troutdale, Oreg.

Filed Mar. 3, 1970, Ser. No. 16,272
Int. Cl. A01h 5/12
U.S. Cl. Plt.—52 1 Claim

The present invention relates to a new and distinct variety of honey-locust tree of the species botanically known as *Gleditsia triacanthos inermis* which was discovered by me on my cultivated property at Englishtown, N.J., as a newly found seedling of unknown parentage.

At the time of my discovery aforesaid, I was growing on my property a block of unnamed and unpatented honey-locust seedlings of unknown parentage, but of the species *Gleditsia triacanthos inermis*. During my cultivation and care of these seedlings, my attention was attracted to one particular tree which exhibited a phenomenal rate of growth far surpassing that of all the other seedlings in the same block and being grown under identical conditions. In the early years of its growth, the trunk caliper of this tree, as measured one foot above the ground, consistently doubled the diameter of the other trees.

Continued observations of these seedlings, and of progeny derived therefrom by budding, over a prolonged period of time fully confirmed the aforementioned growth habit of my new seedling, as well as established other outstanding characteristics thereof. Together, these characteristics, as briefly enumerated in the following summary, represent a unique and commercially valuable combination which distinguishes my new honey locust from all other varieties of which I am aware:

(1) An unusually rapid rate of growth substantially double that in trunk caliper size in comparison with the normal rate for the species *Gleditsia triacanthos inermis*, particularly during its early years;
(2) A dense branching habit, with the lateral branches extending inwardly of the tree to give it a greater fullness and less pendulous form than is usually typical of the species;
(3) A round-headed tree form; and
(4) Attractive green foliage which becomes yellow in the fall season.

Asexual reproduction of my new honey locust variety, as performed on my behalf by budding at Troutdale, Oreg., shows that the foregoing characteristics and distinctions are established and transmitted through succeeding propagations.

The accompanying drawing shows a typical tree specimen of my new honey locust at the age of about ten years and depicting its general form and fall foliage color, and also shows a typical foliage specimen on a somewhat larger scale and depicting the normal foliage color during the growing season.

While the exceptionally vigorous habit of growth, dense and round-headed tree form and attractive foliage color are the principal distinctive features of my new variety of honey locust tree, and it otherwise is typical of the species *Gleditsia triacanthos inermis*, the following brief detailed description is given for convenience, with color terminology in accordance with Koster's Color Guide, except where general color terms of ordinary dictionary significance are obvious:

Parentage: A newly found seedling of an unnamed honey-locust variety of unknown parentage, but of the species *Gleditsia triacanthos inermis*.
Propagation: Holds its distinguishing characteristics through succeeding propagations by budding.
Locality where grown and observed: Englishtown, N.J. and Troutdale, Oreg.
Tree: Vigorous; exceptionally rapid grower; large; upright; dense; round-headed; hardy.
*Trunk.*—Stocky; smooth.
*Branches.*—Stocky; smooth.
*Color.*—Green.
*Lenticels.*—Normal for the species.
Foliage: Normal for the species.
*Shape.*—Pinnate.
*Color.*—Near Taxus Green, Plate 81 (Koster), turning to near Apricot, Plate 11 (Koster) in the fall season.
*Petiole.*—Medium length.
*Glands.*—Normal for the species.
Flower buds: Normal for the species.
Flowers: Normal for the species.
Seeds: Normal for the species.

I claim:

1. A new and distinct variety of honey-locust tree of the species botanically known as *Gleditsia triacanthos inermis*, substantially as herein shown and described, characterized particularly as to novelty by the unique combination of an unusually rapid rate of growth substantially double that in trunk caliper size in comparison with the normal rate for the species *Gleditsia triacanthos inermis*, particularly during its early years, a dense branching habit, with the lateral branches extending inwardly of the tree to give it a greater fullness and less pendulous form than is usually typical of the species, a round-headed tree form, and attractive green foliage which becomes yellow in the fall season.

No references cited.

ROBERT E. BAGWILL, Primary Examiner